US010335441B2

United States Patent
Shimizu et al.

(10) Patent No.: US 10,335,441 B2
(45) Date of Patent: Jul. 2, 2019

(54) ORAL COMPOSITION CONTAINING BIFIDOBACTERIA AND CRUCIFEROUS VEGETABLE

(71) Applicant: SUNSTAR INC., Osaka (JP)

(72) Inventors: Yasumitsu Shimizu, Osaka (JP); Kanetada Shimizu, Kanagawa (JP)

(73) Assignee: SUNSTAR INC., Osaka (JP)

( * ) Notice: Subject to any disclaimer, the term of this patent is extended or adjusted under 35 U.S.C. 154(b) by 121 days.

(21) Appl. No.: 15/506,470

(22) PCT Filed: Aug. 26, 2015

(86) PCT No.: PCT/JP2015/074082
§ 371 (c)(1),
(2) Date: Feb. 24, 2017

(87) PCT Pub. No.: WO2016/031880
PCT Pub. Date: Mar. 3, 2016

(65) Prior Publication Data
US 2017/0246225 A1  Aug. 31, 2017

(30) Foreign Application Priority Data

Aug. 26, 2014 (JP) ................. 2014-171484

(51) Int. Cl.
*A61K 35/745* (2015.01)
*A61K 47/46* (2006.01)
*A61K 36/31* (2006.01)
*A61K 9/00* (2006.01)
*A61K 9/16* (2006.01)
*A61K 9/20* (2006.01)
*A23L 2/02* (2006.01)

(52) U.S. Cl.
CPC .............. *A61K 35/745* (2013.01); *A23L 2/02* (2013.01); *A61K 9/0053* (2013.01); *A61K 9/0095* (2013.01); *A61K 9/16* (2013.01); *A61K 9/1611* (2013.01); *A61K 9/2018* (2013.01); *A61K 9/2054* (2013.01); *A61K 36/31* (2013.01); *A61K 47/46* (2013.01); *A23V 2002/00* (2013.01)

(58) Field of Classification Search
CPC .... A61K 35/745; A61K 9/0053; A61K 36/31; A23L 2/02; A23V 2002/00
See application file for complete search history.

(56) References Cited

U.S. PATENT DOCUMENTS

2012/0171167 A1  7/2012  Kondo et al.
2014/0369965 A1  12/2014 Herranz et al.

FOREIGN PATENT DOCUMENTS

| EP | 1 064 855 | 1/2001 |
|----|-----------|--------|
| JP | 11-266860 | 10/1999 |
| JP | 2000-333670 | 12/2000 |
| JP | 2006-34262 | 2/2006 |
| JP | 2011-517568 | 6/2011 |
| JP | 2014-505467 | 3/2014 |
| WO | 2009/127566 | 10/2009 |
| WO | 2011/034166 | 3/2011 |

OTHER PUBLICATIONS

International Search Report dated Nov. 17, 2015 in International (PCT) Application No. PCT/JP2015/074082.
Notification of Reasons for Refusal dated Apr. 3, 2018 in Japanese Application No. 2014-171484, with Machine Translation.

*Primary Examiner* — Kade Ariani
(74) *Attorney, Agent, or Firm* — Wenderoth, Lind & Ponack, L.L.P.

(57) ABSTRACT

Further enhancement in useful effects of *Bifidobacteria*. An oral composition comprising (A) *Bifidobacterium breve* MCC1274 (FERM BP-11175) and (B) at least one cruciferous vegetable selected from the group consisting of broccoli and cabbage.

10 Claims, 2 Drawing Sheets

Fig. 1

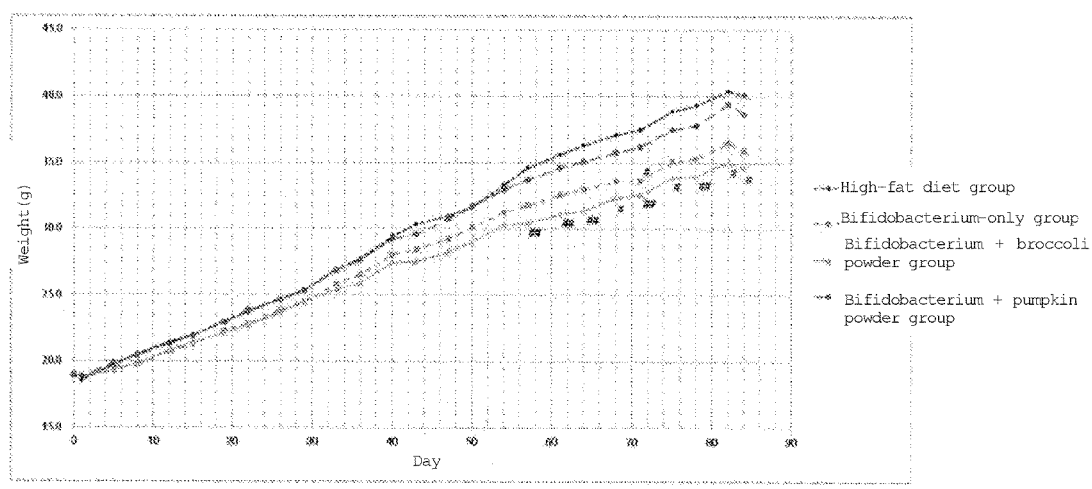

Evaluation of functional component using obese mice induced by high-fat diet  – Changes in weight –
Each value is an average of 10 samples
# represents p<0.05, ## represents p<0.01 (There is a significant difference from HFD group according to Dunnett's multiple test.)

Fig. 2

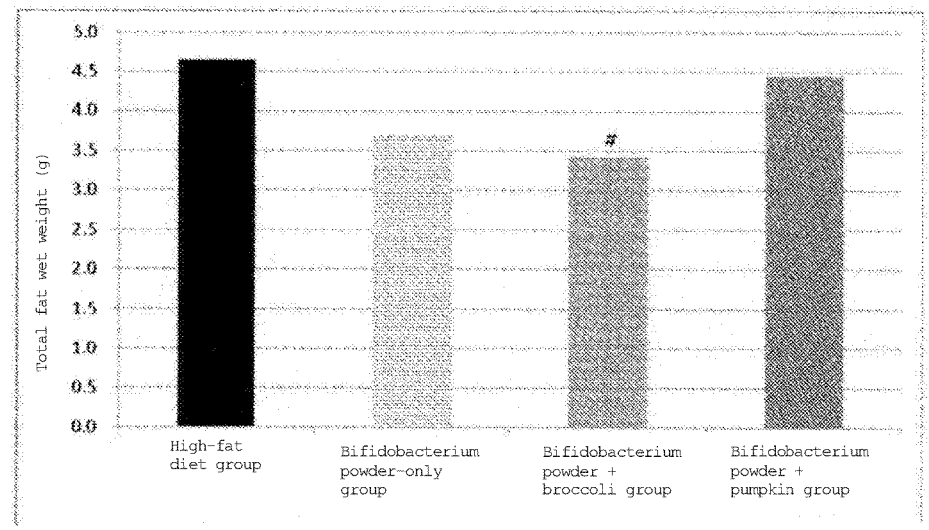

Evaluation of functional component using obese mice induced by high-fat diet – Total fat wet weight –
Each value is an average of 10 samples
# represents p<0.05 (There is a significant difference from HFD group according to Dunnett's multiple test.)

Evaluation of functional component using obese mice induced by high-fat diet
- Bifidobacteria proportion -

Evaluation of functional component using obese mice induced by high-fat diet
- Changes in weight (effects of broccoli) -
Each value is an average of 8 samples

ORAL COMPOSITION CONTAINING BIFIDOBACTERIA AND CRUCIFEROUS VEGETABLE

TECHNICAL FIELD

The present invention relates to an oral composition containing a specific *Bifidobacteria* and a specific cruciferous vegetable.

BACKGROUND ART

Bacteria belonging to genus *Bifidobacterium* (hereinafter referred to as "*Bifidobacteria*") are known for their various favorable activities as intestinal bacteria. With a recent increase in health consciousness, many *Bifidobacteria*-containing foods have been on the market in the attempt to use the superior nature of *Bifidobacteria*.

Some types of *Bifidobacteria* have particularly superior anti-obesity effects. For example, Patent Document 1 discloses that *Bifidobacterium breve*, which has a low ability to convert into conjugated linoleic acid, has anti-obesity effects and glucose tolerance improvement effects without depending on conjugate linoleic acid.

There have been ongoing searches for further superior effects of *Bifidobacteria* and consideration of methods for enhancing the effects of *Bifidobacteria*.

CITATION LIST

Patent Documents

Patent Document 1: WO2011/034166 pamphlet

SUMMARY OF INVENTION

Technical Problem

An object of the present invention is to further enhance the useful effects of *Bifidobacteria*.

Solution to Problem

The inventors of the present invention found that, by using a combination of a specific *Bifidobacteria* and a specific cruciferous vegetable, it is possible to enhance anti-obesity effects of the *Bifidobacteria*. The inventors conducted further improvement based on this finding and completed the present invention.

For example, the present invention encompasses the subject matters according to the items below.

Item 1. An oral composition comprising:
 (A) *Bifidobacterium breve* MCC1274 (FERM BP-11175); and
 (B) at least one cruciferous vegetable selected from the group consisting of broccoli and cabbage.

Item 2. A method for enhancing anti-obesity effects of an oral composition by using a combination of *Bifidobacterium breve* MCC1274 (FERM BP-11175) and at least one cruciferous vegetable selected from the group consisting of broccoli and cabbage in the composition.

Item 3. An oral composition for anti-obesity, comprising:
 (A) *Bifidobacterium breve* MCC1274 (FERM BP-11175); and
 (B) at least one cruciferous vegetable selected from the group consisting of broccoli and cabbage.

Item 4. A diet method comprising taking an oral composition, the oral composition comprising:
 (A) *Bifidobacterium breve* MCC1274 (FERM BP-11175); and
 (B) at least one cruciferous vegetable selected from the group consisting of broccoli and cabbage.

Advantageous Effects of Invention

The present invention uses a combination of *Bifidobacterium breve* MCC1274 (FERM BP-11175), which is a kind of *Bifidobacteria*, and at least one cruciferous vegetable selected from the group consisting of broccoli and cabbage, thereby enhancing the anti-obesity effect of the *Bifidobacteria*. In particular, the present invention significantly enhances the anti-obesity effects of *Bifidobacteria* despite the fact that the anti-obesity effects of *Bifidobacteria* cannot be easily enhanced because the effects will not be enhanced simply by increasing the number of *Bifidobacteria*.

Further, since the vegetable used with *Bifidobacteria* for the enhancement is at least one cruciferous vegetable selected from the group consisting of broccoli and cabbage, and since the vegetable is frequently used as food, it is possible to easily obtain superior anti-obesity effects by orally taking a composition comprising the *Bifidobacteria* and the cruciferous vegetable.

BRIEF DESCRIPTION OF DRAWINGS

FIG. 1 shows results of an examination using obese mice induced by high-fat diet for examining anti-obesity effects by intake of *Bifidobacteria* and vegetable. More specifically, FIG. 1 shows changes in weight of mice (average of n=10) fed with a combination of high-fat feed, *Bifidobacteria* (*Bifidobacterium breve* MCC1274 powder), and/or vegetable powder (broccoli powder or pumpkin powder). # and ## indicate a significant difference from the high-fat feed group (Group A) according to Dunnett's multiple test, wherein # represents $p<0.05$, and ## represents $p<0.01$.

FIG. 2 shows results of an examination using obese mice induced by high-fat diet for examining anti-obesity effects by intake of *Bifidobacteria* and a vegetable. More specifically, FIG. 2 shows total fat wet weight of mice (average of n=10) fed with a combination of high-fat feed, *Bifidobacteria* (*Bifidobacterium breve* MCC1274 powder), and/or vegetable powder (broccoli powder or pumpkin powder). #($p<0.05$) indicates cases with a significant difference from the high-fat feed group (Group A) according to Dunnett's multiple test.

FIG. 3 shows *Bifidobacteria* proportion relative to the total bacterial amount in feces of mice (average of n=10) fed with a combination of high-fat feed, *Bifidobacteria* (*Bifidobacterium breve* MCC1274 powder), and/or vegetable powder (broccoli powder or pumpkin powder).

FIG. 4 shows changes in weight of mice (average of n=8) fed with a combination of high-fat feed, *Bifidobacteria* (*Bifidobacterium breve* MCC1274 powder), and/or vegetable powder (broccoli powder or pumpkin powder).

DESCRIPTION OF EMBODIMENTS

Figure 3:
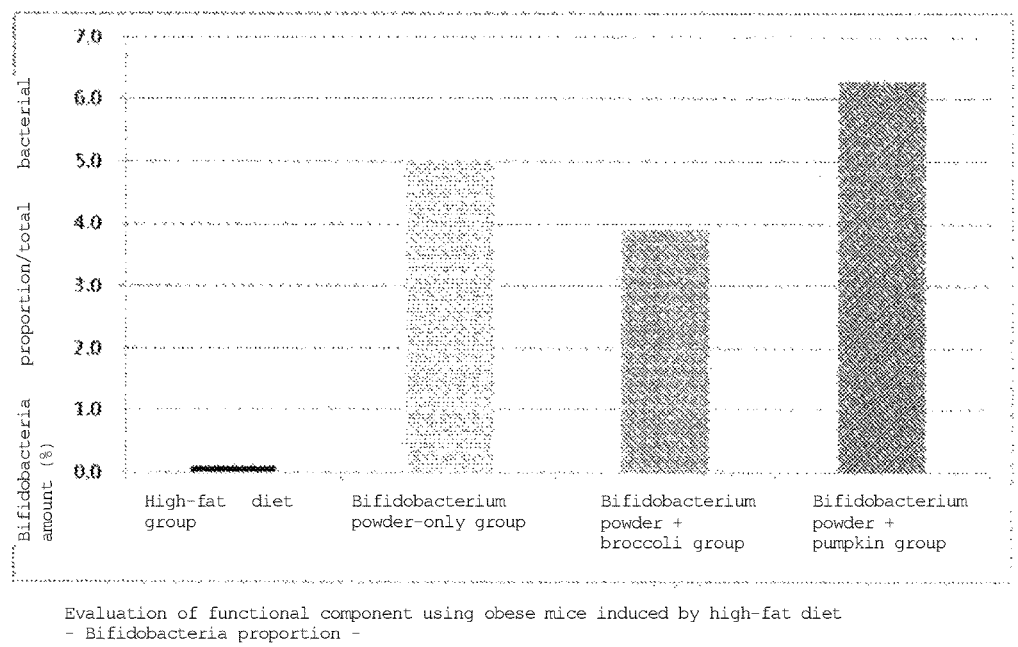
FIG. 3 shows results of an examination using obese mice induced by high-fat diet for examining anti-obesity effects by intake of *Bifidobacteria* and a vegetable. More specifically.

The present invention is more specifically explained below.

The present invention relates to an oral composition comprising a specific *Bifidobacteria* and a specific cruciferous vegetable.

The *Bifidobacterium* contained in the oral composition of the present invention is *Bifidobacterium breve* MCC1274. Insofar as the effects of the present invention are not impaired, the oral composition of the present invention may also contain one or more other kinds of *Bifidobacteria*. *Bifidobacterium breve* MCC1274 is a bacterium belonging to genus *Bifidobacteria*, and was obtained and identified by one of the applicants of the present application according to the procedures disclosed in WO2011/034166. The bacterium has been deposited with the International Patent Organism Depositary, National Institute of Advanced Industrial Science and Technology (Central 6, 1-1-1 Higashi, Tsukuba, Ibaraki 305-8566 Japan) since Aug. 25, 2009, under accession No. FERM BP-11175. The International Patent Organism Depositary in the National Institute of Advanced Industrial Science and Technology was consolidated with the International Patent Organism Depositary in the Incorporated Administrative Agency National Institute of Technology and Evaluation (NITE) in April 2012, and their responsibility regarding the Patent Organism Depositary was taken over by the International Patent Organism Depositary in the Biological Resource Center of the National Institute of Technology and Evaluation (NITE-IPOD) (Room 120, 2-5-8 Kazusa-Kamatari, Kisarazu-city, Chiba 292-0818 Japan).

The cruciferous vegetable contained in the oral composition of the present invention is at least one member selected from the group consisting of broccoli and cabbage. The broccoli used for the present invention is a Mediterranean native plant of genus *Brassica*, which is a kind of green and yellow vegetables and is also called midori-hana yasai (green flower vegetables) or me-hana yasai (bud flower vegetables) (scientific name: *Brassica oleracea* var. *italica*). Examples includes Asli, Anfree, Erude, Endeavour, Castle, Green Parasol, Green Beauty, Green Voice, Green Face, Green Veil, Green Comet, Green Dome, Green Palace, Charade, Shuster, Stick Senor, Three Seven, Three Main, Challenger, Heights, Paragreen, Big Dome, Pixel, Forest, First Star, Burosutemu, Marshall, Mega Dome, Egao, Kizuna, Subaru, Nozomi, Yume, Yumemori, Yutaka, Yayoi, TBR434, Nakate No. 2, Shikimidori, Maimidori, Sachiyoshi, Sairin, Ryokurin, Kairei, Raimei, Ryokuen, Ryokutei, Ryokuteki, Ryokurei, and the like. Examples of the portions used for the present invention include flower buds (i.e., buds of inflorescence and stems, terminal buds, and lateral buds), Broccoli sprouts (stems, leaves, and cotyledon and hypocotyl immediately after germination), stems, and leaves. Among these, flower buds and broccoli sprouts are preferable, and flower buds are most preferable. The cabbage used in the present invention is a European native plant of genus *Brassica*, which mostly has a head shape and is also called Kanran or Tamana (scientific name: *Brassica oleracea* var. *capitata*). Examples include Early Time, Early Ball, Green Kid, Green Ball (Marukyu), Red Rookie, Red Cabbage, Petit Vert, Purple Cabbage, Chirimen Cabbage (Savoy Cabbage, Glad, Shukumen Kanran), Amadama, Shiosai, Shizuhama, Harune, Misaki, Bud Cabbage, Misaki Kanran, Raiyo, Gakuyo, Kandaiko, Kinshun, Seiryu, Jyunpu, Sinran, Ogosho, Toyohikari, Ranten, Reiho, Seirin, FuyuSuruga, Fuyudama, Sapporo Daikyu, and the like. Examples of the portions used for the present invention include leaves and stems. In the present invention, the broccoli and cabbage are used in the form of pulverized matter (including dried matter), juice (including dried matter) and fragments obtained by freeze drying. The pulverized matter means a processed product in the form of puree or paste. More specifically, pulverized matter means a product obtained by processing a vegetable into a puree or paste using a pulverizer or a strainer such as Comitrol processor, a Masscolloider, a food processor, a pulper finisher, or the like. In pulverizing vegetables, blanching in hot water is performed as necessary for cleaning, cutting of stem ends, peeling, and enzyme deactivation. "Juice" means a low-viscosity liquid. More specifically, juice is obtained by directly squeezing vegetables and filtering it as necessary, or compressing or centrifuging the pulverized matter and filtering it as necessary. Insofar as the effects of the present invention are not impaired, one or more other kinds of cruciferous plants may be contained.

The oral composition of the present invention may be in the form of a solid, such as powder, granule, pills, tablets, flakes, capsules, blocks, or bars. The oral composition of the present invention may have a different form insofar as *Bifidobacterium breve* MCC1274 is present in the composition as live bacteria. Further, any fermented compositions may be suitably used regardless of the form. A solid form is preferable because it has a high likelihood of maintaining the living state of *Bifidobacterium breve* MCC1274 for a long time. A formulation that enables *Bifidobacterium breve* MCC1274 to reach the bowel in the form of live bacteria is further preferable. The content of *Bifidobacterium breve* MCC1274 (may hereinafter be referred to as "the *Bifidobacteria*") in the oral composition of the present invention is, but not particularly limited to, about $10^6$ to $10^{12}$ CFU/g, preferably about $10^7$ to $10^{11}$ CFU/g, most preferably about $10^8$ to $5 \times 10^{10}$ CFU/g. "CFU" is an abbreviation for colony forming units.

Further, when the oral composition is a solid form that does not substantially contain water, the total content of the at least one member selected from the group consisting of broccoli and cabbage is preferably 0.05 g/10 g or more, more preferably 0.1 g/10 g or more, based on the entire amount of the oral composition of the present invention on a dry mass basis in a state that the composition contains normal-temperature-insoluble solids content. The "solid form" means, as stated above, for example, powder, granule, pills, tablets, flakes, blocks, capsules, and the like. When the oral composition has a form other than a solid form, the content is preferably 5 g/100 g or more, more preferably 10 g/100 g or more in a state that the composition contains normal-temperature-insoluble solids content. When the oral composition is in a state that normal-temperature-insoluble solids are removed, the content is preferably 2.5 g/100 g or more, more preferably 5 g/100 g or more.

The step for producing the oral composition of the present invention may comprise a fermentation step. When the oral composition is produced through a fermentation step, it is preferable to use a pulverized matter or juice of broccoli or the like. Before the fermentation step is performed, a heat sterilization step may be performed as necessary so as to ensure a stable fermentation step.

Further, since some bacteria are not easily killed by heat sterilization, the pH of the oral composition that does not have a solid form is preferably 4.6 or less. In this case, in view of taste of the oral composition, it is more preferable to decrease the pH of the oral composition by using acids generated by the fermentation.

When the fermentation is performed, *Bifidobacterium breve* MCC1274 is used in the form of a *Bifidobacteria* starter, which is prepared in advance. The *Bifidobacteria* starter is prepared by a standard method. The properties, composition, preparation method of the starter are not particularly limited. The *Bifidobacteria* starter may be a liquid, a frozen matter, or powder.

The *Bifidobacteria* starter in the form of a liquid is obtained by a culture using MRS Broth, reconstituted skim milk containing yeast extract, glucose/yeast extract medium, or the like. The frozen *Bifidobacteria* starter is obtained by directly freezing the *Bifidobacteria* starter in a liquid form, or concentrating the *Bifidobacteria* by centrifugation and freezing the resulting matter.

The powdery *Bifidobacteria* starter is obtained by either directly freeze-drying the *Bifidobacteria* starter in a liquid form, or concentrating the *Bifidobacteria* starter using a centrifugal apparatus and then freeze-drying the resulting matter, thereby producing powder. These starters are usable regardless of the property but preferably have liquid forms before being added.

In the case of frozen and powdery *Bifidobacteria* starters, after the bacteria are inoculated, it may take more time for the *Bifidobacteria* to proliferate and start fermentation, compared with liquid *Bifidobacteria* starters. In this case, by inoculating the starter into the composition after the starter is proliferated in liquid medium and is thereby turned into a liquid, it is possible to cancel such delay of fermentation start time.

Further, powdery starters may need more time to be dispersed when the starters are added to the composition, compared with liquid starters. However, it is possible to add water sterilized in advance to the powdery starter. The amount of the *Bifidobacteria* starter to be inoculated into the composition to be subjected to the fermentation is preferably at least $10^6$ CFU or more, more preferably $10^7$ CFU or more, per gram of the total composition to be fermented.

Further, the number of *Bifidobacteria* in the *Bifidobacteria* starter may be appropriately adjusted according to the amount of the *Bifidobacteria* starter or the amount of the composition to be fermented. In particular, for a liquid starter, the number of the *Bifidobacteria* to be inoculated is $10^8$ CFU or more, or $10^9$ CFU or more, per gram of the composition to be fermented.

The liquid temperature of the composition when the *Bifidobacteria* starter is inoculated is 25° C. to 45° C., preferably 30° C. to 40° C., and more preferably 34° C. to 38°.

The termination point of the fermentation may be determined by measuring the lactic acid acidity and pH. During the lactic fermentation of the composition of the present invention, terminal lactic acid acidity at which the increase in acidity of lactic acid stopped, and terminal pH at which the decrease in pH stopped are observed as the termination point of the fermentation for each type, brand, or origin of the vegetable. When the drying step is not performed after the fermentation step, stopping fermentation before reaching the terminal point of the fermentation, i.e., before reaching the terminal lactic acid acidity and the terminal pH, is not preferable because it may result in variation in lactic acid acidity and pH of the oral composition, or a failure to obtain sufficient fermentation metabolites. This may further result in a failure to obtain uniform quality of the oral composition. Generally, the fermentation time is 12 hours to 72 hours, preferably 16 hours to 36 hours. Fermented oral compositions that were not subjected to a drying step are preferably stored or distributed in a refrigerated or frozen state.

When the fermentation of *Bifidobacteria* is not performed, it is preferable to use dried pulverized matter, dried juice, or a mixture thereof, of broccoli or the like. When the fermentation of *Bifidobacteria* is performed, it is preferable to use pulverized matter, juice, or a mixture thereof.

For an oral composition in a solid form, it is possible to dry a fermented composition or a composition obtained by evenly mixing all components; however, it is more preferable to separately dry broccoli or the like and the *Bifidobacteria*, mix them in a solid state, and process the mixture into a predetermined formulation. When components other than the broccoli or the *Bifidobacteria* are incorporated in the composition, it is preferable to mix them with broccoli or the like and then dry the mixture, or separately dry the components and broccoli or the like and then incorporate them in the composition.

Further, the oral composition of the present invention is preferably designed to contain about $10^8$ to $10^{10}$ CFU of *Bifidobacterium breve* MCC1274 as a daily dose for an adult, and at least one member selected from the group consisting of broccoli and cabbage in an amount of about 0.3 to 6 g on a dry mass basis in a state that the composition contains normal-temperature-insoluble solids content, or in an amount of about 0.15 to 3 g in a state that normal-temperature-insoluble solids are removed.

The oral composition of the present invention ensures superior anti-obesity effects. In particular, the oral composition of the present invention ensures superior body weight gain inhibition effects and body fat gain inhibition effects. Therefore, the oral composition of the present invention may be preferably used for dieting (slimming), cosmetic purposes, body weight gain inhibition, body fat gain inhibition, body weight control, shape maintenance (in particular after birth and while breastfeeding), and the like, particularly for diet foods or cosmetic purposes.

The oral composition of the present invention may contain components other than the *Bifidobacteria* and broccoli or cabbage insofar as the effects of the present invention are not adversely affected. Examples of the components include pharmacologically acceptable carriers and carriers acceptable based on the Food Sanitation Law.

The oral composition of the present invention may be used preferably as a pharmaceutical composition, a food additive composition (i.e., a composition used by being added to another food composition or food material when cooking or eating), or a food composition. When the oral composition of the present invention is a pharmaceutical composition, the composition contains, in addition to the *Bifidobacteria* and cruciferous vegetable, pharmaceutically acceptable bases, carriers, additives (for example, solvents, dispersants, emulsifiers, buffer agents, stabilizers, excipients, binders, disintegrants, lubricant, and the like) or the like as necessary and is preferably prepared into a pharmaceutical preparation such as pills, round tablets, powdered drug, liquids, suspensions, emulsions, granules, or capsules in accordance with ordinary procedures.

Further, when the oral composition of the present invention is a food additive composition, the composition may contain, in addition to the *Bifidobacteria* and broccoli or cabbage, bases acceptable based on the food sanitation law, carriers, additives or other known components or materials used as food additives. Further, examples of the forms of the food additive composition include, but not particularly limited to, freeze-dried solid, powder, flakes, granules, or blocks; more specifically, seasonings, spices, furikake (dried food sprinkled over rice), treats such as cake or ice cream, topping materials for canapes, and beverage additives (for example, beverage additives to be dissolved or dispersed in milk). These food additive compositions may be prepared in accordance with ordinary procedures.

Further, when the oral composition of the present invention is a food composition, the composition is obtained by, for example, incorporating bases acceptable based on the food sanitation law, carriers, additives or other components or materials used as food, in addition to in addition to the *Bifidobacteria* and broccoli or cabbage. In particular, examples of such compositions include anti-obesity (more specifically, body weight gain inhibition, fat gain inhibition, or the like) processed food, beverages, health food (food with nutrient function claims, food for specified health use, or the like), supplements, and patient food. Examples of specific food form include, but not particularly limited to, compressed molded food forms such as tablets, pills, flakes, and snack-like forms, capsules such as soft capsules, hard capsule, microcapsules, or coated solids, dairy products such as yogurt, solid beverages to be dissolved in liquids such as water, granule beverages, powder beverages, as well as granular food and thin flake food that are directly eaten.

So as to inhibit the extinction of *Bifidobacterium breve* MCC1274 used for the present invention after the intake, it is preferable to process the oral composition of the present invention to impart an enteric function The present invention includes a method for enhancing anti-obesity effects (including a method for enhancing slimming effects) by using *Bifidobacterium breve* MCC1274 (FERM BP-11175) together with at least one cruciferous vegetable selected from the group consisting of broccoli and cabbage in an oral composition, and a method for producing an anti-obesity oral composition by using a similar combination.

Further, the present invention also encompasses a method for enhancing anti-obesity effects of *Bifidobacterium breve* MCC1274 (FERM BP-11175) by using *Bifidobacterium breve* MCC1274 (FERM BP-11175) together with at least one cruciferous vegetable selected from the group consisting of broccoli and cabbage. The method preferably excludes therapeutic methods; in particular, the method is preferably a method duly performed without involving healthcare professionals.

Further, the present invention also encompasses an obesity prevention method or a slimming care method that is performed by taking *Bifidobacterium breve* MCC1274 (FERM BP-11175) and at least one cruciferous vegetable selected from the group consisting of broccoli and cabbage. The oral composition described above may be preferably used in these methods.

Further, the method is preferably designed to take about $10^8$ to $10^{10}$ CFU of *Bifidobacterium breve* MCC1274 as a daily dose for an adult, and at least one member selected from the group consisting of broccoli and cabbage in an amount of about 0.3 to 6 g on a dry mass basis in a state that the composition contains normal-temperature-insoluble solids content, or in an amount of about 0.15 to 3 g in a state that normal-temperature-insoluble solids are removed.

EXAMPLES

The present invention is more specifically explained below; however, the present invention is not limited to those examples.

Preparation of *Bifidobacterium breve* MCC1274 Powder (Bacteria Powder) *Bifidobacterium breve* MCC1274 was provided by Morinaga Milk Industry Co., Ltd. *Bifidobacterium* with a specified number of bacteria, i.e., $5\times10^{10}$ CFU/g, was used.

Consideration of Evaluation Regarding Anti-Obesity Effects

Male mice C57BL/6NCr1Crj (SPF) at 5 weeks of age were purchased from Charles River Laboratories International, Inc., followed by seven-day habituation and quarantine during the period from the arrival to the start of test. The mice were divided into four groups (A to D, each having ten mice) on Day 7. The mice in each group were allowed free access to high-fat feed D12492 (60 kcal %, Research Diet Inc.). Further, in addition, the mice in group B were fed with *Bifidobacterium breve* MCC1274 powder, the mice in group C were fed with *Bifidobacterium breve* MCC1274 powder and broccoli powder, and the mice in group D were fed with *Bifidobacterium breve* MCC1274 powder and pumpkin powder. Specifically, each group was fed as follows.

Group A: High-fat diet feed
Group B: High-fat diet feed+*Bifidobacterium breve* MCC1274 powder
Group C: High-fat diet feed+*Bifidobacterium breve* MCC1274 powder+broccoli powder
(broccoli powder: Domestic broccoli powder produced by Kodama Foods Co., Ltd.)
Group D: High-fat diet feed+*Bifidobacterium breve* MCC1274 powder+pumpkin powder
(Pumpkin powder: Nippon Funmatsu Yakuhin Co., Ltd. pumpkin powder)

The dose of *Bifidobacterium breve* MCC1274 powder was 10 mg (corresponding to $5\times10^8$ CFU) and the dose of vegetable powder was 100 mg/30 g of body weight per day. They were placed in an injection syringe (disposable syringe, Terumo Corporation) equipped with a feeding needle and were orally administered to mice once a day.

The administration was conducted for 84 days. The body weight of each mouse was measured twice a week, and the feed intake amount was measured once a week, thereby determining the total amount of seven days. Further, after the administration period, the mice were killed, and perirenal fat, posterior abdominal wall fat, and epididymis region fat were isolated, and their wet weights were measured. Further, the total value of perirenal fat, posterior abdominal wall fat, and epididymis region fat was evaluated as the total fat wet weight. Furthermore, their feces were obtained on Day 84, and the proportion of *Bifidobacteria* relative to the total bacteria amount in the feces was measured by outsourcing to TechnoSuruga Laboratory Co., Ltd (real time PCR).

FIG. 1 shows the results of the measurement of body weight of each mice group during the administration period. FIG. 2 shows the results of the measurement of total fat wet weight in each mice group. Further, FIG. 3 shows results of measurement of proportion of *Bifidobacteria* relative to the total bacteria amount in the feces in each mice group.

As is evident from FIG. 1, in comparison with Group A (administration of high-fat diet), although the body weight gain was inhibited in Group B (administration of only *Bifidobacteria* powder), the statistical significance was observed only on Day 71. However, in Group C (administration of a combination of *Bifidobacteria* and broccoli), a significant difference from Group A (high-fat diet group) was observed in the measurements on Day 57 and thereafter, thereby showing significant body weight reduction effects. In contrast, results of Group D (administration of a combination of *Bifidobacteria* and pumpkin powder) showed a decrease in the effects of *Bifidobacteria*, thereby clarifying that the effects vary depending on the vegetables used with *Bifidobacteria*.

In FIG. 2, similarly to the body weight gain inhibition effects (see FIG. 1), a statistical significance in terms of fat weight was observed only in Group C (administration of a combination of *Bifidobacteria* and broccoli).

In FIG. 3, the proportion of *Bifidobacteria* was decreased in Group C (administration of a combination of *Bifidobacteria* and broccoli) compared with Group B (administration of only *Bifidobacteria* powder). In contrast, the proportion of *Bifidobacteria* was increased in Group D (administration of a combination of *Bifidobacteria* and pumpkin powder) in which anti-obesity effects (body weight reduction effects, fat gain inhibition effect) were not observed.

The results suggested that an increase in proportion of *Bifidobacteria* does not always result in enhancement of anti-obesity effects. It was strongly suggested that broccoli does not simply increase the proportion of *Bifidobacteria*, but may be capable of enhancing the anti-obesity effects of *Bifidobacteria*. In addition to the anti-obesity effects of *Bifidobacteria*, the metabolism of the vegetable in the body is assumed to have effects on body weight reduction.

Consideration of the Evaluation of Anti-Obesity Effects of Broccoli (Reference Example)

Male mice C57BL/6NCrlCrj (SPF) at 5 weeks of age were purchased from Charles River Laboratories International, Inc., followed by seven-day habituation and quarantine during the period from the arrival to the start of test. The mice were divided into three groups (Group α, Group β, and Group γ, each having eight mice) on Day 7. The mice in each group were allowed free access to high-fat feed D12492 (60 kcal %, Research Diet Inc.). Further, in addition, mice in Group γ were orally administered 10 mg (corresponding to $5 \times 10^8$ CFU) of *Bifidobacterium breve* MCC1274 powder once a day using an injection syringe (disposable syringe, Terumo Corporation) equipped with a feeding needle. Further, mice in Group β were fed with high-fat feed in which about 5 mass % of broccoli was added in advance. Specifically, each group was fed as follows.

Group α: High-fat diet feed
Group β: High-fat diet feed+broccoli powder
Group γ: High-fat diet feed+*Bifidobacterium breve* MCC1274 powder The administration was conducted for 56 days. The body weight of each mouse was measured twice a week and the feed intake amount was measured once a week, thereby determining the total amount of seven days. The amount of broccoli powder ingested by the mice in Group β was calculated based on the feed intake, which was found to be about 150 mg/day.

Figure 4:
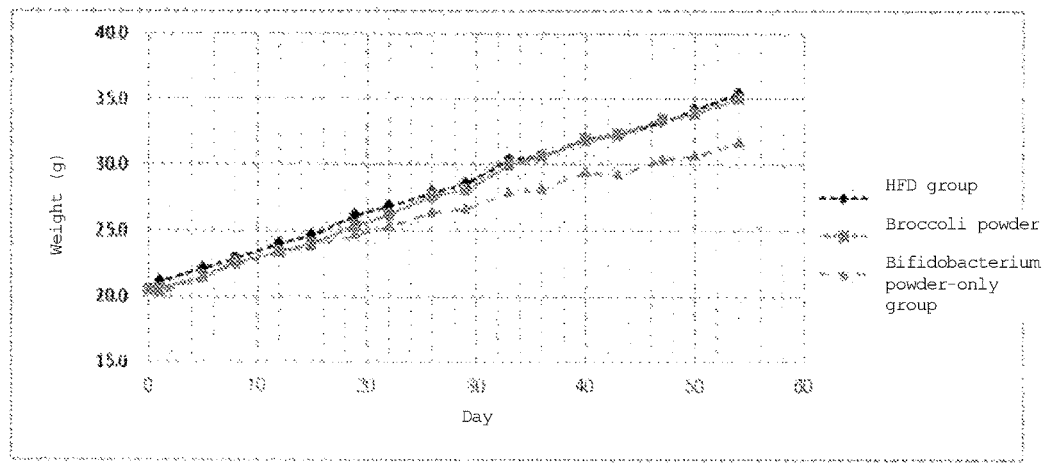
FIG. 4 shows results of an examination using obese mice induced by high-fat diet for examining anti-obesity effects by intake of *Bifidobacteria* and a vegetable. More specifically.

FIG. 4 shows the results of measurement of body weight of the mice in each group during the administration period. In FIG. 4, Group α is referred to as "HFD group," Group β is referred to as "broccoli powder," and Group γ is referred to as "a group of sole administration of *Bifidobacteria*." The results of FIG. 4 revealed that the body weight gain inhibition effects were hardly observed in Group β (a broccoli powder group), and it was thus assumed that the body weight gain inhibition effects cannot be obtained by sole use of broccoli. Although the body weight gain inhibition effects were observed in Group γ (group of sole administration of *Bifidobacteria*), a statistical significance (Dunnett's multiple comparison test) was not confirmed.

Formulation Examples

Formulation Examples of the oral composition of the present invention are shown below.

Formulation Example 1: Powder Preparation (5 g/Bag)

| | |
|---|---|
| Broccoli powder | 3.4 g |
| Cabbage powder | 1.0 g |
| Galacto-oligosaccharide | 0.5 g |
| *Bifidobacterium breve* MCC1274 powder ($>1 \times 10^{10}$ CFU/g) | 0.1 g |

Raw materials excluding the *Bifidobacteria* powder are granulated and the *Bifidobacteria* is added. The resulting powder is sealed in a predetermined container.

Formulation Example 2: Tablet (1 g/Tablet, 3 to 5 Tablets Per Day)

| | |
|---|---|
| Palatinit | 0.42 g |
| Crystalline cellulose | 0.1 g |
| Broccoli powder | 0.40 g |
| Sucrose fatty acid ester | 0.03 g |
| *Bifidobacterium breve* MCC1274 powder ($>1 \times 10^{10}$ CFU/g) | 0.05 g |

Formulation Example 3: Powder Preparation (3 g/Bag)

| | |
|---|---|
| *Bifidobacterium breve* MCC1274-fermented broccoli freeze-dried powder | 2.5 g (number of bacteria: $1 \times 10^9$ CFU/bag) |
| Milk oligosaccharides | 0.5 g |
| Silicon dioxide | Very small amount |

After the materials are fully mixed, the powder is sealed in a predetermined container.

Formulation Example 4: Frozen Drink

| | |
|---|---|
| *Bifidobacterium breve* MCC1274-fermented broccoli puree | 20 g |
| Broccoli puree | 15 g |
| Cabbage juice | 10 g |
| Apple juice | 5 g |
| Lemon juice | 0.5 g |
| Purified water | 49.5 g |
| | (amount per 100 g) |

160 g of the formulation is placed in a container, and immediately frozen and stored.

The invention claimed is:

1. An anti-obesity oral composition, comprising: a combination of (A) freeze-dried *Bifidobacterium breve* MCC 1274 (FERM BP-11175); and (B) broccoli powder, wherein the anti-obesity effects of *Bifidobacterium breve* MCC 1274 (FERM BP-11175) are enhanced.

2. A method for enhancing anti-obesity effects of *Bifidobacterium breve* MCC 1274 (FERM BP-11175), the method comprising: combining broccoli powder with freeze-dried *Bifidobacterium breve* MCC 1274 (FERM BP-11175), thereby enhancing the anti-obesity effects of said *Bifidobacterium breve* MCC 1274 (FERM BP-11175).

3. The anti-obesity oral composition according to claim 1, wherein the content of (A) freeze-dried *Bifidobacterium breve* MCC 1274 in the oral composition is about $10^6$ to $10^{12}$ CFU/g.

4. The anti-obesity oral composition according to claim 1, wherein the oral composition has a solid form, and the total content of the (B) broccoli powder is 0.05 g/10 g or more based on the entire amount of the oral composition on a dry mass basis.

5. The anti-obesity oral composition according to claim 1, wherein the oral composition has a form other than a solid form, and the total content of the (B) broccoli powder is 5 g/100 g or more based on the entire amount of the oral composition.

6. A diet or an anti-obesity method comprising administering an oral composition comprising: a combination of (A) freeze-dried *Bifidobacterium breve* MCC 1274 (FERM BP-11175); and (B) broccoli powder.

7. The method according to claim 6, wherein the content of (A) *Bifidobacterium breve* MCC1274 in the oral composition is about $10^6$ to $10^{12}$ CFU/g.

8. The method according to claim 6,
wherein the oral composition has a solid form, and
the total content of the (B) broccoli powder is 0.05 g/10 g or more based on the entire amount of the oral composition on a dry mass basis.

9. The method according to claim 6,
wherein the oral composition has a form other than a solid form, and
the total content of the (B) broccoli powder is 5 g/100 g or more based on the entire amount of the oral composition.

10. The anti-obesity oral composition according to claim 1, wherein the form of the oral composition is at least one selected from the group consisting of a powder, a granule, a pill, a tablet, a flake, a capsule, a block and a bar.

* * * * *